US011691964B2

(12) United States Patent
Lee et al.

(10) Patent No.: US 11,691,964 B2
(45) Date of Patent: *Jul. 4, 2023

(54) CRYSTALLINE FORMS OF PHTHALAZINONE COMPOUND

(71) Applicant: Idience Co., Ltd., Seoul (KR)

(72) Inventors: Kunhee Lee, Seoul (KR); Seoktaek Lee, Seoul (KR); Keuncheol Ryu, Seoul (KR); Hanna Seo, Seoul (KR); Hyeran Yang, Seoul (KR); Wonje Seong, Seoul (KR); Jinyoung Yoon, Seoul (KR)

(73) Assignee: ILDONG PHARMACEUTICAL CO., LTD., Seoul (KR)

(*) Notice: Subject to any disclaimer, the term of this patent is extended or adjusted under 35 U.S.C. 154(b) by 0 days.

This patent is subject to a terminal disclaimer.

(21) Appl. No.: 17/830,756

(22) Filed: Jun. 2, 2022

(65) Prior Publication Data

US 2022/0372020 A1    Nov. 24, 2022

Related U.S. Application Data

(63) Continuation of application No. 16/858,158, filed on Apr. 24, 2020, now Pat. No. 11,390,608.

(60) Provisional application No. 63/013,276, filed on Apr. 21, 2020.

(51) Int. Cl.
   *C07D 403/10* (2006.01)

(52) U.S. Cl.
   CPC ........ *C07D 403/10* (2013.01); *C07B 2200/13* (2013.01)

(58) Field of Classification Search
   CPC ................ C07D 403/10; C07B 2200/13
   See application file for complete search history.

(56) References Cited

U.S. PATENT DOCUMENTS

| 6,627,646 B2 | 9/2003 | Bakale |
| 7,834,015 B2 | 11/2010 | Jones et al. |
| 8,129,380 B2 | 3/2012 | Menear et al. |
| 8,188,084 B2 | 5/2012 | Jones et al. |
| 9,187,430 B2 | 11/2015 | Ji et al. |
| 9,682,973 B2 | 6/2017 | Kang et al. |
| 9,844,550 B2 | 12/2017 | Kang et al. |
| 2005/0059663 A1 | 3/2005 | Martin et al. |
| 2008/0161280 A1 | 7/2008 | Gandhi et al. |
| 2016/0222003 A1 | 8/2016 | Kang et al. |
| 2019/0177281 A1 | 6/2019 | Rajan et al. |

FOREIGN PATENT DOCUMENTS

| CN | 101925595 A | 12/2010 |
| CN | 103130723 A | 6/2013 |
| EP | 1633724 B1 | 3/2006 |
| EP | 2799435 A1 | 11/2014 |
| JP | 2006-519827 A | 8/2006 |
| JP | 2009-538896 A | 11/2009 |
| JP | 2009-538897 A | 11/2009 |
| JP | 2010-514785 A | 5/2010 |
| KR | 20170037116 A | 4/2017 |
| WO | 02/36576 A1 | 5/2002 |
| WO | 03/093261 A1 | 11/2003 |
| WO | 2004/080976 A1 | 9/2004 |
| WO | 2007/138351 A2 | 12/2007 |
| WO | 2007/138355 A1 | 12/2007 |
| WO | 2009/063244 A1 | 5/2009 |
| WO | 2009/112832 A1 | 9/2009 |
| WO | 2012/014221 A1 | 2/2012 |
| WO | 2012/019427 A1 | 2/2012 |
| WO | 2012/019430 A1 | 2/2012 |
| WO | 2012019426 A1 | 2/2012 |
| WO | 2012/071684 A1 | 6/2012 |
| WO | 2012/072033 A1 | 6/2012 |
| WO | 2012071684 A1 | 6/2012 |
| WO | 2013078771 A1 | 6/2013 |

OTHER PUBLICATIONS

International Search Report for Application No. PCT/IB2020/000324 dated Jan. 18, 2021.
Written Opinion of International Patent Application No. PCT/IB2020/000324 dated Jan. 18, 2021.
Lee, et al., "Development of IDX-1197, a novel, selective, and highly potent PARP inhibitor," 28th AACR-NCI-EORTC Molecular Targets and Cancer Therapeutics Conference in Philadelphia, Pennsylvania, USA; Oct. 26-30, 2017.
Tajbakhsh, et al., "Catalyst-Free One-Pot Reductive Alkylation of Primary and Secondary Amines and N,N-Dimethylation of Amino Acids Using Sodium Borohydride in 2,2,2-Trifluoroethanol," Synthesis, (2011), No. 3: 0490-0496.
Lee, et al., "A comparative preclinical study of PARP inhibitors demonstrates superb properties for IDX-1197," AACR Annual Meeting 2018, Apr. 14-18, 2018, Chicago, Illinois, USA.
CMU Pharmaceutical polymorphism, internet, p. 1-3 (2002) printout Apr. 3, 2008.
Singhai et al., "Drug Polymorphism, etc.," Advanced Drug Delivery reviews 56, p. 335-347 (2004).
Concise Encyclopedia Chemistry, NY, Walter de Gruyter, 1993, pp. 872-873.
Jain et al., "Polymorphism in Pharmacy," Indian Drugs, 1986, 23(6), 315-329.
Muzaffar et al., "Polymorphism and Drug Availability, etc.," Journal of Pharm., Lahore, 1979, 1(1) pp. 59-66.
U.S. Pharmacopia # 23, National Formulary # 18, 1995, pp. 1843-1844.
Doelker, english translation of S.T.P, Pratiques, 1999, 9(5), 399-409, pp. 1-33.

(Continued)

*Primary Examiner* — Timothy R Rozof
(74) *Attorney, Agent, or Firm* — McBee Moore & Vanik IP, LLC (57) ABSTRACT

The present specification provides crystalline forms of 4-[3-(3-[(cyclopropylamino)methyl]azetidine-1-carbonyl)-4-fluorobenzyl]phthalazin-1(2H)-one hydrochloride, methods of preparing the same, and pharmaceutical compositions comprising the same.

5 Claims, 8 Drawing Sheets

(56) References Cited

OTHER PUBLICATIONS

Doelker, english translation of Ann. Pharm. Fr., 2002, 60: 161-176, pp. 1-39.
Faday et al., "Using Tetrahertz, etc.," Journal of Pharm. Sci., 92(4), 2003, pp. 831-838.
Otuska et al., "Effect of Polumorphic, etc.," Chem. Pharm. Bull., 47(6), 1999, pp. 852-856.
Zhu, et al., "Discovery and SAR of orally efficacious tetrahydropyridopyridazinone PARP inhibitors for the treatment of cancer," Bioorganic & Medicinal Chemistry, (2012), vol. 20, No. 15:4635-4645.
Pinedo et al., "Translational Research: The Role of VEGF in Tumor Angiogenesis," The Oncologist, (2000), vol. 5, (Suppl 1): 1-2.
McMahon "VEGF Receptor Signaling in Tumor Angiogenesis," The Oncologist, (2000), vol. 5, (Suppl. 1): 3-10.
Ye et al., "Design, Synthesis, and Biological Evaluation of a Series of Benzo[de][1,7]naphthyridin-7(8H)-ones Bearing a Functionalized Longer Chain Appendage as Novel PARP1 Inhibitors," J. Med. Chem., 2013, 56:2885-2903.

CRYSTALLINE FORMS OF PHTHALAZINONE COMPOUND

CROSS REFERENCE TO RELATED APPLICATION

This application is a continuation of U.S. application Ser. No. 16/858,158, filed 24 Apr. 2020, which claims priority to U.S. Application No. 63/013,276 filed 21 Apr. 2020, the contents of which are incorporated herein by reference in their entirety.

TECHNICAL FIELD

The present invention relates to crystalline forms of a phthalazinone compound of Formula 1, methods of preparing the same, and pharmaceutical compositions including the same. More particularly, the present invention relates to crystalline forms of 4-[3-(3-[(cyclopropylamino)methyl]azetidine-1-carbonyl)-4-fluorobenzyl]phthalazin-1(2H)-one hydrochloride, methods of preparing the same, and pharmaceutical compositions including the same.

[Formula 1]

BACKGROUND ART OF INVENTION

U.S. Pat. No. 9,682,973 ("US'973") discloses 4-[3-(3-[(cyclopropylamino)methyl]azetidine-1-carbonyl)-4-fluorobenzyl]phthalazin-1(2H)-one of Formula 2 and pharmaceutically acceptable salts thereof having anti-cancer activity as poly(ADP-ribose) polymerase (hereinafter referred to as "PARP") inhibitors:

[Formula 2]

The compound of Formula 1, which is a hydrochloride of the compound of Formula 2, is also disclosed in US'973.

US'973 discloses a method of preparing the hydrochloride compound of Formula 1 from the compound of Formula 2. In particular, after the compound of Formula 2 is dissolved in dichloromethane and then cooled down to 0° C., a 1 N HCl aqueous solution is added thereto, stirred at room temperature for 1 hour, and concentrated, to prepare the compound of Formula 1.

However, when trying to conduct a scale-up process based on the method disclosed in US'973, the compound of Formula 1 was obtained in a viscous oil phase, not crystalline solid. Such an oil phase has low purity and stability compared to a crystalline solid, and is less desirable for commercial production. Further, since the method according to US'973 requires a concentration process, this method may not be preferred for the commercial large-scale production of a medicinal drug substance.

Furthermore, the preparation method of US'973 uses dichloromethane as a solvent, which may remain as a residual impurity even after removal. As a result, the preparation method of US'973 could potentially be less desirable in terms of safety due to strict maximum requirements of the solvent.

DISCLOSURE

Technical Problem

One aspect of the present invention is to provide a crystalline form of 4-[3-(3-[(cyclopropylamino)methyl]azetidine-1-carbonyl)-4-fluorobenzyl]phthalazin-1(2H)-one hydrochloride, which has improved stability and purity and which is more suitable for mass (i.e., commercial or large-scale) production.

Another aspect is to provide a pharmaceutical composition containing the crystalline form of 4-[3-(3-[(cyclopropylamino)methyl]azetidine-1-carbonyl)-4-fluorobenzyl]phthalazin-1 (2H)-one hydrochloride.

Another aspect is to provide a method of preparing a crystalline form of 4-[3-(3-[(cyclopropylamino)methyl]azetidine-1-carbonyl)-4-fluorobenzyl]phthalazin-1 (2H)-one hydrochloride.

Other objectives and advantages of the present invention will become apparent from the following detailed descriptions along with the appended claims. Certain content not described in the present specification may be sufficiently recognized and inferred by those skilled in the art or similar fields of the present invention, and thus description thereof is omitted.

Technical Solution

In one aspect of the present invention, there is provided crystalline form of a compound of Formula 1, characterized in exhibiting an X-ray powder diffraction (XRPD) pattern comprising peaks at 2θ±0.2° values of 13.7°, 15.9°, and 24.1°:

[Formula 1]

In another aspect, there is provided a pharmaceutical composition comprising a crystalline form of the compound of Formula 1 as an active ingredient and at least one pharmaceutically acceptable carrier or diluent.

In another aspect, there is provided a method of preparing a crystalline form of the compound of Formula 1, the method comprising:

dissolving 4-[3-(3-[(cyclopropylamino)methyl]azetidine-1-carbonyl)-4-fluorobenzyl]phthalazin-1(2H)-one in one or more solvents selected from a group consisting of a $C_1$-$C_3$ alcohol, acetone, ethyl acetate, and methyl t-butyl ether; and adding a hydrochloric acid solution.

In accordance with the present invention, in an embodiment, the method does not involve the use of a concentration process. As such, the present method would be more preferable for a commercial mass process.

In another aspect, there is provided a crystalline form of the compound of Formula 1 prepared by the above-described method.

BRIEF DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Hereinafter, the present invention will be described in greater detail. Unless otherwise defined, all technical terms used in the present invention have the same meaning as commonly understood by those skilled in the related art of the present invention.

The contents of all publications cited as reference documents herein are incorporated in the present specification by reference in their entirety.

Descriptions and embodiments disclosed in one portion of the present invention may be applied to other descriptions and embodiments in other portions of the present invention. That is, all combinations of various elements disclosed in the present invention belong within the scope of the present invention. Additionally, the scope of the present invention should not be limited by the specific descriptions described herein below.

In addition, although a preferred method or sample is described in the specification, those similar or equivalent thereto fall within the scope of the present invention. In addition, the term "comprising" is intended to have an open-ended meaning and permits the inclusion of additional elements that are not identified.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. As used herein, the term "about" refers to being within 5% of a particular value or range, and more preferably within 1% to 2%. For example, "about 10%" refers to 9.5% to 10.5%, and preferably, 9.8% to 10.2%. For another example, "about 100° C." refers to 95° C. to 105° C., and preferably, 98° C. to 102° C.

Unless otherwise specified, it should be apparent to a skilled person in the art that the values of peaks from X-ray powder diffraction studies reported in this application are associated with experimental errors typically observable in this field. Specifically, a peak is interpreted to be located within the angle variation±0.5° of the value reported herein. Preferably, a peak is interpreted to be located within the angle variation±0.2° of the value reported herein, more preferably, within the angle variation±0.1°.

Crystalline Forms of Compound of Formula 1

One aspect of the present invention provides a crystalline form of the compound of Formula 1 below, characterized in exhibiting an X-ray powder diffraction (XRPD) pattern comprising peaks at diffraction angles 2θ±0.2° values of 13.7°, 15.9°, and 24.1°.

[Formula 1]

Hereinafter, the crystalline form is referred to as Crystalline Form A.

In one aspect, Crystalline Form A may exhibit an XRPD pattern comprising peaks at three or more and, preferably four or more, 2θ±0.2° values selected from the group consisting of 9.1°, 11.9°, 13.2°, 13.7°, 15.9°, 16.8°, 18.1°, 23.2°, 24.1°, 25.5°, and 26.6°.

In particular, Crystalline Form A may exhibit an XRPD pattern comprising peaks at 2θ±0.2° values of 9.1°, 13.2°, 13.7°, 15.9°, 16.8°, 24.1°, and 26.6°.

In more particularity, Crystalline Form A may exhibit an XRPD pattern comprising peaks at 2θ±0.2° values of 9.1°, 11.9°, 13.2°, 13.7°, 15.9°, 16.8°, 18.1°, 23.2°, 24.1°, 25.50, and 26.60.

The XRPD pattern may be obtained when irradiated with a Cu-Kα light source, for example, using a D8 Advance (Bruker ASX, Germany) analyzer. The Cu-Kα light source may have the wavelength of 1.54056 Å.

These peaks may be those having a relative intensity ($I/I_o$) of about 10%, more specifically, about 15% or greater.

Crystalline Form A may have an exothermic peak which has a starting point at about 219° C. and its highest point at about 225° C. in a differential scanning calorimetry (DSC, 10° C./min). Crystalline Form A may have an exothermic peak at about 222±4° C. in a DSC (10° C./min).

Crystalline Form A may have, in a thermogravimetric analysis (TGA), a weight loss of 4% or less at the temperature of up to 100° C., and may decompose at or above 200° C.

In another aspect of the present invention, Crystalline Form A of the compound of Formula 1 may be in a substantially pure form.

The term "substantially pure" as used herein means at least 95% purity, preferably 97% purity, or more preferably 99% purity, wherein 95% purity means no more than 5%, 97% purity means no more than 3%, and 99% purity means no more than 1%, of any other form of the compound of Formula 1 (other crystalline form, amorphous form, and so forth) being present.

In one embodiment, Crystalline Form A of the compound of Formula 1 may have 95% or greater purity in crystalline form.

Crystalline Form A of the compound of Formula 1 was found to have significantly improved storage stability and purity (see Experimental Example 1). According to long-term stability purity test of Experimental Example 1, about 0.20 wt % of total impurities were found in Crystalline Form A after 24 months at 25±2° C. Therefore, Crystalline Form A of the compound of Formula 1 enables preparation of medicines having improved stability.

Furthermore, Crystalline Form A of the compound of Formula 1 may be prepared to have a higher safety profile. Dichloromethane was used as a solvent in the previous method of preparing the compound of Formula 1. Dichloromethane is very toxic and is classified as a Class 2 solvent, i.e., a solvent that is regulated in medicines at residual amounts of 600 ppm or less according to the International Council for Harmonization (ICH) guideline Q3C [Guideline on Impurities for Residual Solvents]. However, it is difficult to lower the amount of residual solvents, as expensive treatment processes are required. Therefore, Crystalline Form A of the compound of Formula 1 has the advantage of being safer and more economical in terms of production for use as a medicinal drug substance.

Method of Preparing Crystalline Form A of the Compound of Formula 1

Another aspect of the present invention provides a method of preparing Crystalline Form A of the compound of Formula 1.

In one embodiment, the method comprises steps of:
dissolving 4-[3-(3-[(cyclopropylamino)methyl]azetidine-1-carbonyl)-4-fluorobenzyl]phthalazin-1(2H)-one in one or more solvents selected from a group consisting of a $C_1$-$C_3$ alcohol, acetone, ethyl acetate, and methyl t-butyl ether; and
adding a hydrochloric acid solution.

In another embodiment, the method comprises steps of:
dissolving 4-[3-(3-[(cyclopropylamino)methyl]azetidine-1-carbonyl)-4-fluorobenzyl]phthalazin-1 (2H)-one in one or more solvents selected from a group consisting of a $C_1$-$C_3$ alcohol, acetone, ethyl acetate, and methyl t-butyl ether to obtain a mixture;
cooling the mixture;
adding a hydrochloric acid solution;
raising the temperature to about room temperature, cooling, and stirring to obtain a solid; and
filtering, washing, and drying the solid.

In another embodiment, the method comprises steps of:
(a) dissolving 4-[3-(3-[(cyclopropylamino)methyl]azetidine-1-carbonyl)-4-fluorobenzyl]phthalazin-1(2H)-one in one or more solvents selected from a group consisting of a $C_1$-$C_3$ alcohol, acetone, ethyl acetate, and methyl t-butyl ether to obtain a mixture;
(b) cooling the obtained mixture to about 0° C.;
(c) adding, to the mixture, a hydrochloric acid solution, optionally, together with a mixture of a hydrochloric acid solution and one or more solvents selected from a group consisting of a $C_1$-$C_3$ alcohol, acetone, ethyl acetate, and methyl t-butyl ether;
(d) raising the temperature to about room temperature;
(e) stirring the mixture for about 10 to about 14 hours;
(f) cooling the mixture to about 10 to about 20° C.;
(g) stirring the cooled mixture for about 20 to about 60 minutes to obtain a solid; and
(h) filtering, washing, and drying the solid.

In step (a), 4-[3-(3-[(cyclopropylamino)methyl]azetidine-1-carbonyl)-4-fluorobenzyl]phthalazin-1(2H)-one, i.e., the compound of Formula 2, may be dissolved in one or more solvents selected from a group consisting of a $C_1$-$C_3$ alcohol, acetone, ethyl acetate, and methyl t-butyl ether, and subsequently cooled down to about 0° C. accordingly to step (b), and thereafter step (c) may be performed. The solvent may be, for example, a single solvent, such as methanol, ethanol, isopropyl alcohol, acetone, ethyl acetate, and methyl t-butyl ether, or a mixed solvent thereof, e.g., a mixed solvent of methanol and methyl t-butyl ether.

The free base form of the compound of Formula 1, that is, 4-[3-(3-[(cyclopropylamino)methyl]azetidine-1-carbonyl)-4-fluorobenzyl]phthalazin-1 (2H)-one, may be prepared according to the methods disclosed in US'973, the disclosure of which is incorporated herein in its entirety by reference. However, the embodiments described herein are not limited thereto, and the free base form of the compound of Formula 1 may be prepared using any method known to the person of ordinary skill in the relevant art.

In the present preparation method, specifically, in step (c), the hydrochloric acid solution may be added as a solution in a solvent of water, alkyl acetate (e.g., ethyl acetate, etc.), alkyl ether (e.g., diethyl ether, etc.), or alkyl alcohol (e.g., isopropyl alcohol, ethyl alcohol, etc.). In one specific embodiment, the solvent may be water, ethyl acetate, diethyl ether, isopropyl alcohol, or ethyl alcohol. More specifically, the hydrochloric acid solution may be about 30 to 40%, e.g., 37.0% aqueous solution, 1.0 M solution in ethyl acetate, 1.0 M solution in diethyl ether, 5 to 6 N solution in isopropyl alcohol, or 1.25 M solution in ethyl alcohol.

The amount of the hydrochloric acid in the hydrochloric acid solution or the mixed solution of the hydrochloric acid solution and the solvent may be about 1.0 to about 2.0 equivalents with respect to 1 equivalent of the free base form of the compound of Formula 1. The volume of the hydrochloric acid solution or the mixed solution may be in a ratio (v/w) of about 0.1:1 to about 20:1 with respect to the weight of the free base form of the compound of Formula 1. The solvent in step (c) may be one or more selected from a group consisting of a C1-C3 alcohol, acetone, ethyl acetate, and methyl t-butyl ether.

In step (f), the cooling temperature may be from about 10° C. to about 20° C., and preferably from about 12° C. to about 17° C., and more preferably about 15° C. When stirred, after the cooling, for about 20 minutes to about 60 minutes, and more preferably about 30 to 40 minutes in step (g), Crystalline Form A in a solid phase may be obtained.

Thereafter, filtering, washing, and drying may be performed in step (h).

The washing and drying steps are not specifically limited. The washing may be performed using the solvent used in step (a). The drying may be performed using any method which does not affect the stability of the crystalline form of the compound of Formula 1, for example, at a temperature of about 40° C. to about 50° C. for about 15 hours to 30 hours.

Figure 5:
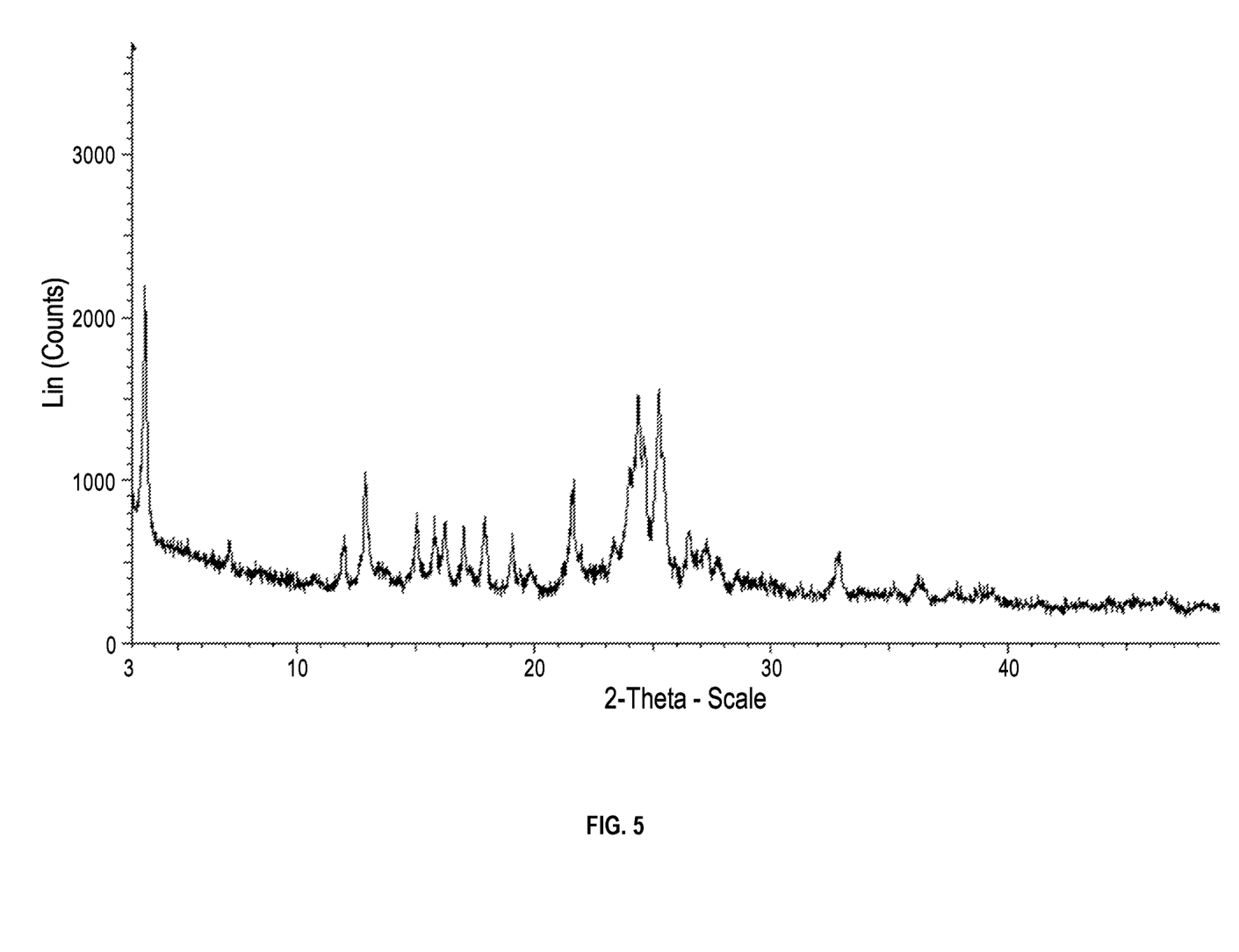
FIG. 5 shows an XRPD pattern of crystalline form C of 4-[3-(3-[(cyclopropylamino)methyl]azetidine-1-carbonyl)-4-fluorobenzyl]phthalazin-1 (2H)-one hydrochloride.

In the case where solvents other than those described above are used for crystallization, another crystalline form may be obtained. For example, when dichloromethane or a mixture of dichloromethane and methanol is used as a solvent, Crystalline Form C of Formula 1 is obtained. Crystalline Form C may exhibit an XRPD pattern comprising peaks at diffraction angles (2θ)±0.2° of 3.5°, 7.1°, 12.9°, 21.6°, 24.4°, and 25.3°. The XRPD pattern of Crystalline Form C is shown in FIG. 5.

Figure 8:
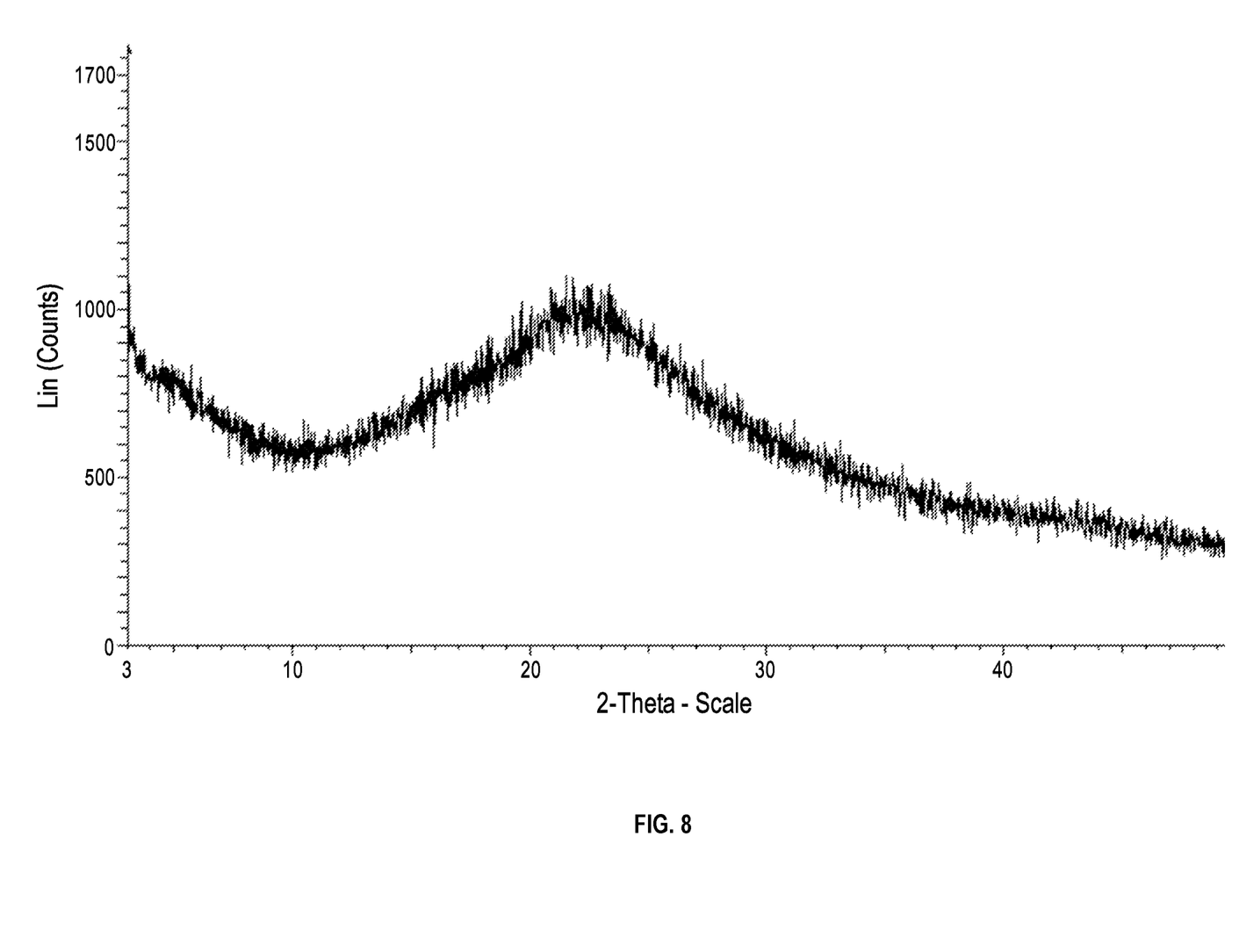
FIG. 8 shows an XRPD pattern of an amorphous form of 4-[3-(3-[(cyclopropylamino)methyl]azetidine-1-carbonyl)-4-fluorobenzyl]phthalazin-1 (2H)-one hydrochloride.

In another example, an amorphous form is obtained by a process comprising steps: completely dissolving a compound of Formula 1 in HCl salt in an excess amount of methanol, concentrating the solvent, rapidly adding acetone to the residual to obtain a crystal, followed by concentrating the solvent, dispersing and stirring the residual solid in n-Heptane, and filtering. The XRPD pattern of the amorphous form is shown in FIG. 8.

Medical Usage and Pharmaceutical Composition

Another aspect of the present invention provides a pharmaceutical composition comprising Crystalline Form A of the compound of Formula 1 as an active ingredient and at least one pharmaceutically acceptable carrier or excipient.

The pharmaceutical composition may comprise about 80% or greater, preferably about 90% or greater, more preferably about 95% or greater, and most preferably about 99% or greater of Crystalline Form A of the compound of Formula 1 with respect to a total amount of the compound of Formula 1. The remainder may be in any other form of the compound of Formula 1 (other possible crystalline forms, amorphous form, and so forth).

As disclosed in US'973, the compound of Formula 1 was found to exhibit PARP inhibitory activity and have anticancer activity, and therefore can be used in the treatment of cancer caused, specifically, by defective DNA-damage repair, or a genetic defect in the BRCA1, BRCA2, or ERG fusion genes. As used herein, the term "genetic defect" may include, but is not limited to, a genetic mutation or lack (deficiency) of a gene, or a defect in gene expression.

The pharmaceutical composition may be used for the treatment of cancer.

The cancer may be caused by defective DNA-damage repair, or a genetic defect in the BRCA1, BRCA2, or ERG fusion gene. For example, the cancer may be selected from the group consisting of breast cancer, ovarian cancer, pancreatic cancer, gastric cancer, lung cancer, colon cancer, brain tumor, prostate cancer, and Ewing's sarcoma. Specifically, the cancer may be breast cancer or ovarian cancer.

When administered to a human patient, a total daily dosage of Crystalline Form A may vary depending on the administration route, administration time, types of other compounds used in combination, or the patient's age, sex, weight, status, medical history, and so forth. Therefore, the dosage of the compound may be determined within the range in which a desired therapeutic effect is achieved without causing harmful or serious adverse effects.

The pharmaceutical composition may be in oral or parenteral dosage form.

For oral dosage forms, the carrier used may include sweetening agents, binders, resolvents, solublizing agents, wetting agents, emulsifying agents, isotonic agents, adsorbents, disintegrating agents, antioxidants, antiseptics, lubricants, fillers, flavoring agents, coating agents, and so forth. For example, the carrier may include lactose, calcium hydrogen phosphate, hydroxypropyl cellulose, carboxymethyl cellulose, colloidal silicon dioxide, fumed silica, magnesium stearate, talc, agar, water, ethanol, polyethylene glycol, polyvinylpyrrolidone, sodium chloride, calcium chloride, orange essence, strawberry essence, vanilla flavor, Opadray white, and so forth.

Examples of available injectable carriers include distilled water, saline, glucose solutions, pseudo-glucose solutions, alcohols, glycol ethers (for example, polyethylene glycol 400), oils, fatty acids, fatty acid esters, glycerides, surfactants, suspending agents, emulsifying agents, and so forth.

Another aspect provides a method for preventing or treating a cancer, comprising administering, to an individual or patient in need of cancer prevention or treatment, a pharmaceutically effective amount of Crystalline Form A of the compound of Formula 1.

The above descriptions of the pharmaceutical composition according to an aspect of the present invention may be applied per se to details of the method for preventing or treating a cancer.

The dose used in the method for preventing or treating a cancer may be an amount effective for the prevention or treatment. The above description of the dose of the pharmaceutical composition may apply per se to the method for preventing or treating a cancer.

The description regarding medical usage and pharmaceutical compositions of the compound of Formula 1 disclosed in US'973 may apply to those of Crystalline Form A of the compound of Formula 1 according to the present invention.

Hereinafter, the present invention will be described in more detail with reference to the following Examples. However, these Examples are for illustrative purposes only, and the invention is not intended to be limited by these Examples.

Analysis Apparatus and Method of Measurement

1. X-Ray Powder Diffraction (XRPD)

X-ray powder diffraction (XRPD) analyses of samples were performed in the range from 3° 2θ to 50° 2θ using a D8 Advance (Bruker ASX, Germany) analyzer. The measurement was performed as follows:

Anode material (Kα): Cu-Kα (1.54056 Å)
Scan range: 3° to 50°
Generator settings: 40 mA, 40.0 kV
Scan speed: 0.5 sec/step Temperature: 20° C.
Step size: 0.02° 2θ
Rotation: no use
2. Differential Scanning Calorimetry (DSC)

Differential scanning calorimetry (DSC) analysis was performed using an AUTO MDSC Q20/RSC40 (TA Instruments) in the temperature range from 25° C. to 300° C. at a heating rate of 5° C./min or 10° C./min. A sample in an amount of 5 mg to 10 mg was weighed and added into an aluminum DSC fan, and the fan was sealed with a perforated aluminum lid in a non-sealing manner. Then, the sample was heated at a scan speed of 5° C./min or 10° C./min from 25° C. to 300° C., and the heat flow reaction generated was monitored in a DSC.

3. Thermal Gravimetric Analysis (TGA)

Thermal gravimetric analysis (TGA) was performed using a TGA Q50 (TA Instruments) in the temperature range from 25° C. to 300° C. at a heating rate of 10° C./min.

4. Gas Chromatography (GC)

Gas Chromatography (GC) was performed using a Agilent 7697A Headspace Sampler/7890A GC Chemstation.

5. Karl Fischer (KF) analysis

Karl Fischer (KF) analysis was performed using (i) Metrohm 795 KFT Titrino System, 795 Key Pad, 703 Ti Stand, and (ii) Mettler Toledo V20S Compact Volumetric KF Titrator.

Preparation Example: Preparation of a Compound of Formula 2

A compound of Formula 2, 4-[3-(3-[(cyclopropylamino)methyl]azetidine-1-carbonyl)-4-fluorobenzyl]phthalazin-1(2H)-one, was prepared according to the process including Steps 1 to 5 as described below.

Step 1. Preparation of tert-butyl 3-[(cyclopropylamino)methyl]azetidine-1-carboxylate 1.0 kg of tert-butyl 3-formylazetidine-1-carboxylate was added into a reactor, and 6.5 kg of trifluoroethanol was added thereto. 0.3 kg of cyclopropylamine was added at 0° C., stirring at ambient temperature for 1 hour, followed by cooling the reactor down to 0° C. 0.2 kg of sodium borohydride was slowly added and stirred at ambient temperature for 1 hour, and then the reactor was cooled down to 0° C. After 10.0 kg of water was slowly added thereto, the reaction mixture was extracted with 6.7 kg of dichloromethane, and the thus-obtained aqueous layer was further extracted with 6.7 kg of dichloromethane. The organic layer was washed with a 15% sodium chloride aqueous solution, treated with 0.5 kg of anhydrous magnesium sulfate, filtered and then concentrated under reduced pressure, to thereby yield 0.98 kg of the titled compound as a yellow oil (Yield: 80.1%). The titled compound was used in a subsequent process without a separate purification process.

$^1$H NMR (CDCl$_3$, 400 MHz) δ 3.99 (t, 2H), 3.60-3.57 (m, 2H), 2.90 (d, 2H), 2.66-2.62 (m, 1H), 2.11-2.06 (m, 1H), 1.59 (br, 1H), 1.44 (s, 9H), 0.46-0.42 (m, 2H), 0.32-0.28 (m, 2H)

Step 2. Preparation of tert-butyl 3-([[[(9H-fluorene-9-yl)methoxy]carbonyl)(cyclopropyl) amino]methyl) azetidine-1-carboxylate 4.0 kg of dichloromethane was added into a reactor, 300.0 g of tert-butyl 3-[(cyclopropylamino)methyl]azetidine-1-carboxylate prepared in Step 1 and 188.4 g of diisopropylethylamine were sequentially added thereto, and then the reactor was cooled down to 0° C. 377.2 g of 9-fluorenylmethoxycarbonyl chloride was slowly added into the reactor such that the internal temperature of the reactor did not exceed 20° C., and the reaction mixture was stirred for 1 hour. 5.0 kg of water was added thereto to wash the organic layer, and the organic layer was further washed with 5.0 kg of a 1 N hydrochloric acid aqueous solution. The organic layer was further washed with a 15% sodium chloride aqueous solution and treated with 250.0 g of anhydrous magnesium sulfate, filtered, and concentrated under reduced pressure, to thereby quantitatively yield 576.7 g of the titled compound as a yellow oil. The titled compound was used in a subsequent process without a separate purification process.

$^1$H NMR (CDCl$_3$, 400 MHz) δ 7.72 (d, 2H), 7.56 (d, 2H), 7.36 (t, 2H), 7.30-7.26 (m, 2H), 4.52 (d, 2H), 4.17 (t, 1H), 3.89-3.85 (m, 2H), 3.56 (m, 2H), 3.30 (m, 2H), 2.60 (m, 1H), 2.28 (m, 1H), 1.43 (s, 9H), 0.61 (m, 2H), 0.45 (m, 2H)

Step 3. Preparation of (9H-fluorene-9-yl)methyl (azetidine-3-ylmethyl)(cyclopropyl)carbamate hydrochloride 1.0 L of ethanol was added into a reactor, 100.0 g of tert-butyl 3-([([(9H-fluorene-9-yl)methoxy]carbonyl)(cyclopropyl)amino]methyl)azetidine-1-carboxylate prepared in Step 2 and 24.8 mL of concentrated hydrochloric acid were sequentially added thereto, and then the resultant mixture was heated. The reaction proceeded at reflux temperature for 30 minutes, and then the reaction mixture was concentrated under reduced pressure. 170 mL of ethyl acetate and 430 mL of n-hexane were added to the residue, stirred at ambient temperature overnight, filtered, and then dried at 40° C., to thereby yield 78.2 g of the titled compound (Yield: 91.2%).

$^1$H NMR (CDCl$_3$, 400 MHz) δ 9.63 (br, 1H), 9.40 (br, 1H), 7.75-7.70 (m, 2H), 7.60-7.55 (m, 2H), 7.38 (t, 2H), 7.32-7.29 (m, 2H), 4.52 (d, 2H), 4.18 (t, 1H), 3.99 (m, 2H), 3.81 (m, 2H), 3.44-3.28 (m, 2H), 2.94 (m, 1H), 2.27 (m, 1H), 0.60-0.59 (m, 2H), 0.43 (m, 2H)

Step 4. Preparation of (9H-fluorene-9-yl)methylcyclopropyl([1-(2-fluoro-5-[(4-oxo-3,4-dihydrophthalazin-1-yl)methyl]benzoyl)azetidine-3-yl]methyl)carbamate

300 mL of dichloromethane was added into a reactor, and 29.8 g of 2-fluoro-5-[(4-oxo-3,4-dihydrophthalazin-1-yl)methyl]benzoic acid and 17.9 g of 1,1'-carbonyldiimidazole were sequentially added thereto. The reaction proceeded at ambient temperature for 1 hour, and then the reactor was cooled down to 15° C. Then, 42.3 g of (9H-fluorene-9-yl)methyl(azetidine-3-ylmethyl)(cyclopropyl)carbamate hydrochloride prepared in Step 3 was added thereto, and 19.4 g of diisopropylamine was slowly added thereto. The reaction mixture was stirred at ambient temperature for 1 hour, 300 mL of water was added thereto to wash the organic layer, and then the organic layer was further washed with a 1 N hydrochloric acid aqueous solution and a 1 N sodium carbonate aqueous solution. The organic layer was further washed with a 5% sodium chloride aqueous solution, treated with 10.0 g of anhydrous magnesium sulfate, filtered, and then concentrated under reduced pressure. 70 mL of ethyl acetate and 350 mL of n-hexane were added to the residue, stirred at ambient temperature overnight, filtered, and then dried at 50° C., to thereby yield 63.2 g of the titled compound (Yield: 91.3%).

$^1$H NMR (DMSO-d6, 400 MHz) δ 12.60 (s, 1H), 8.26-8.24 (m, 1H), 7.97 (d, 1H), 7.90-7.78 (m, 4H), 7.65-7.62 (m, 2H), 7.48-7.28 (m, 7H), 4.51-4.48 (m, 2H), 4.32 (s, 2H), 4.26-4.23 (m, 1H), 3.97-3.86 (m, 2H), 3.62-3.56 (m, 2H), 3.30-3.25 (m, 2H), 2.24 (m, 1H), 1.24-1.23 (m, 1H), 0.48 (m, 2H), 0.38-0.35 (m, 2H)

Step 5. Preparation of 4-[3-(3-[(cyclopropylamino)methyl]azetidine-1-carbonyl)-4-fluorobenzyl]phthalazin-1(2H)-one -continued 150 mL of acetonitrile was added into a reactor, and 30.0 g of (9H-fluorene-9-yl)methylcyclopropyl([1-(2-fluoro-5-[(4-oxo-3,4-dihydrophthalazin-1-yl)methyl]benzoyl)azetidine-3-yl]methyl)carbamate prepared in Step 4 and 34.5 g of piperidine were sequentially added thereto and stirred at ambient temperature for 1 hour. After the reaction mixture was concentrated under reduced pressure, 300 mL of a 2 N hydrochloric acid aqueous solution was added to the residue, stirred for 1 hour, and then filtered through diatomaceous earth. Then, the filtrate was adjusted to pH 9 or greater with a 1 N sodium hydroxide solution and extracted by adding 300 mL of dichloromethane. The aqueous layer was further extracted by adding 300 mL of dichloromethane thereto, and then the organic layer was mixed therewith, washed with a 5% sodium chloride aqueous solution, and then concentrated. 80 mL of methanol and 40 mL of dichloromethane were added to the residue, and then 150 mL of acetone was slowly added thereto. The resulting solid was stirred at ambient temperature overnight, filtered, and dried at 40° C. to yield 17.5 g the titled compound (Yield: 90.1%).

$^1$H NMR (DMSO-$d_6$, 400 MHz) δ 12.62 (s, 1H), 8.27-8.25 (m, 1H), 7.97 (d, 1H), 7.90-7.86 (m, 1H), 7.84-7.79 (m, 1H), 7.46-7.43 (m, 2H), 7.22-7.18 (m, 1H), 4.32 (s, 2H), 4.04-3.56 (m, 4H), 2.73-2.63 (m, 3H), 2.30 (br, 1H), 2.00-1.95 (m, 1H), 0.33-0.12 (m, 4H)

Preparation of Crystalline Form A of Compound of Formula 1

Example 1: Preparation of Crystalline Form A of 4-[3-(3-[(cyclopropylamino)methyl]azetidine-1-carbonyl)-4-fluorobenzyl]phthalazin-1(2H)-one hydrochloride 10.0 mL of methyl alcohol was added to 1.0 g of 4-[3-(3-[(cyclopropylamino)methyl]azetidine-1-carbonyl)-4-fluorobenzyl]phthalazin-1(2H)-one, and mixed and cooled down to 0° C. Subsequently, after 0.2 ml of a 37.0% aqueous hydrochloric acid solution was added thereto, the temperature was raised to room temperature, and the mixture was stirred for 12 hours. After cooling to 15° C., the mixture was additionally stirred for 30 minutes. The obtained solid was then filtered, washed with methyl alcohol, and dried to obtain 0.76 g of Crystalline Form A of 4-[3-(3-[(cyclopropylamino)methyl]azetidine-1-carbonyl)-4-fluorobenzyl] phthalazin-1 (2H)-one hydrochloride (Yield: 69.7%, DSC maximum peak temperature at a heating rate of 10° C./min: 222.81° C.).

Figure 1:
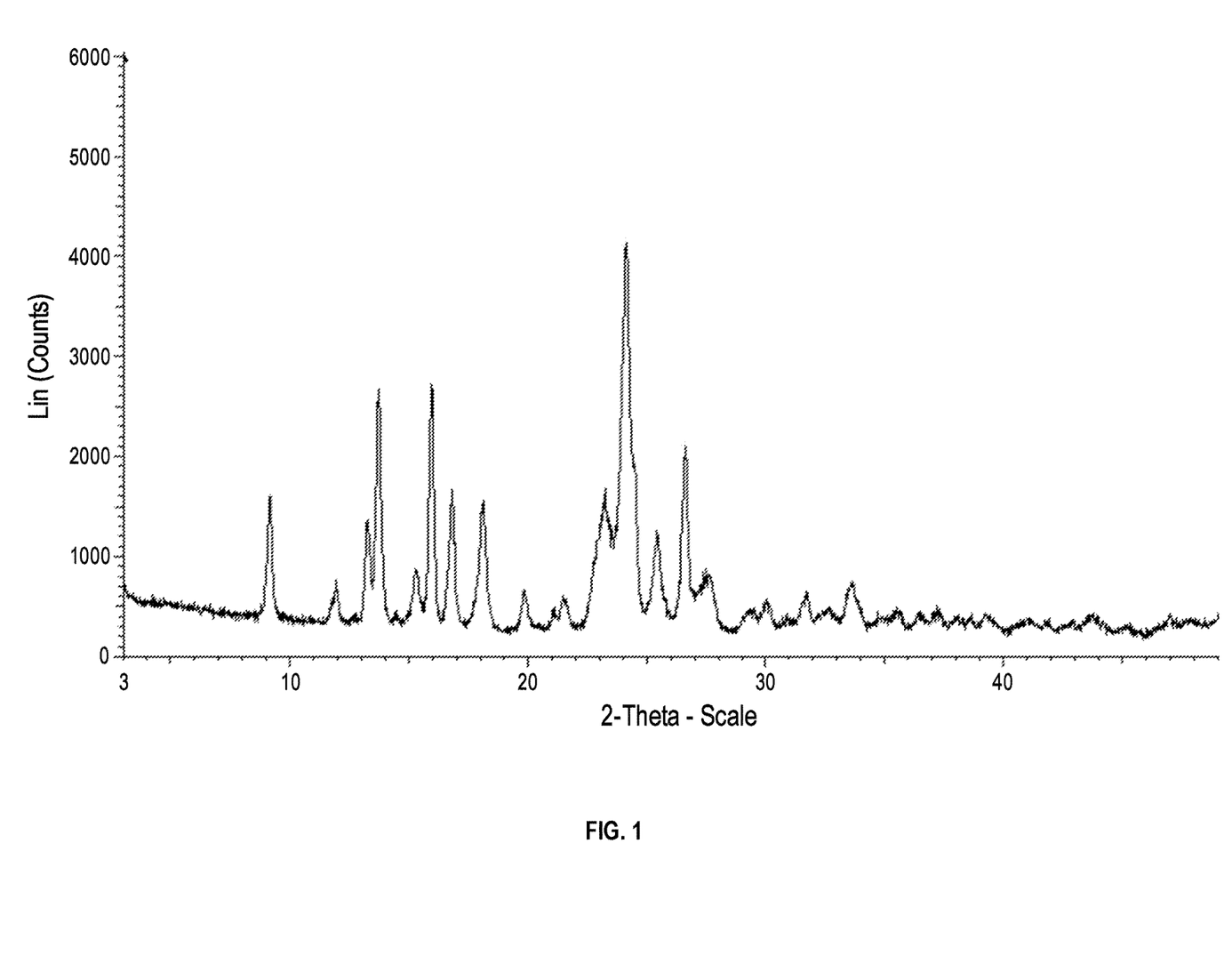
FIG. 1 shows an X-ray powder diffraction (XRPD) pattern of crystalline form A of 4-[3-(3-[(cyclopropylamino)methyl]azetidine-1-carbonyl)-4-fluorobenzyl]phthalazin-1(2H)-one hydrochloride prepared in Example 1.
Figure 2:
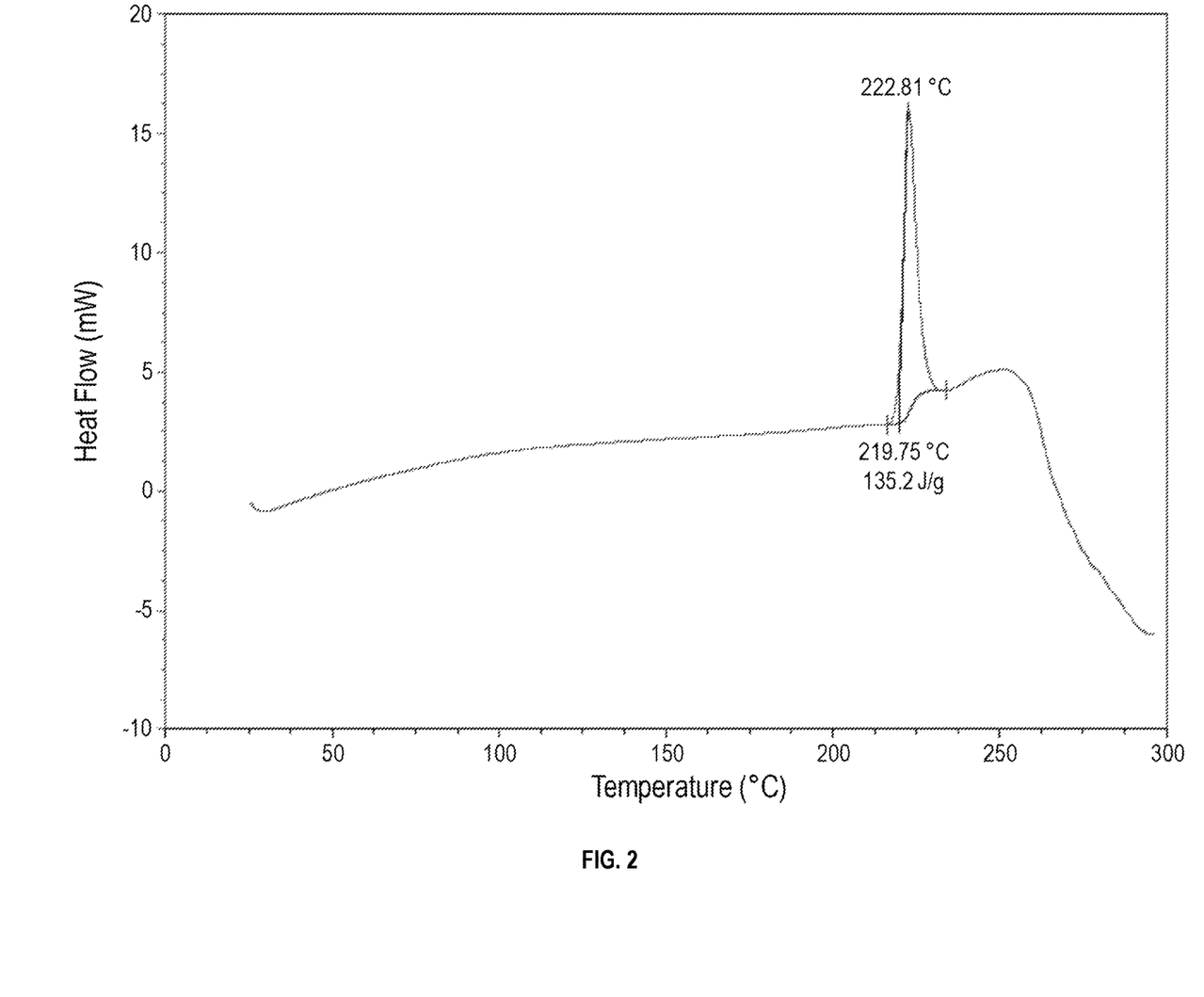
FIG. 2 is a graph illustrating the results of differential scanning calorimetry (DSC) of crystalline form A of 4-[3-(3-[(cyclopropylamino)methyl]azetidine-1-carbonyl)-4-fluorobenzyl]phthalazin-1(2H)-one hydrochloride prepared in Example 1.
Figure 3:
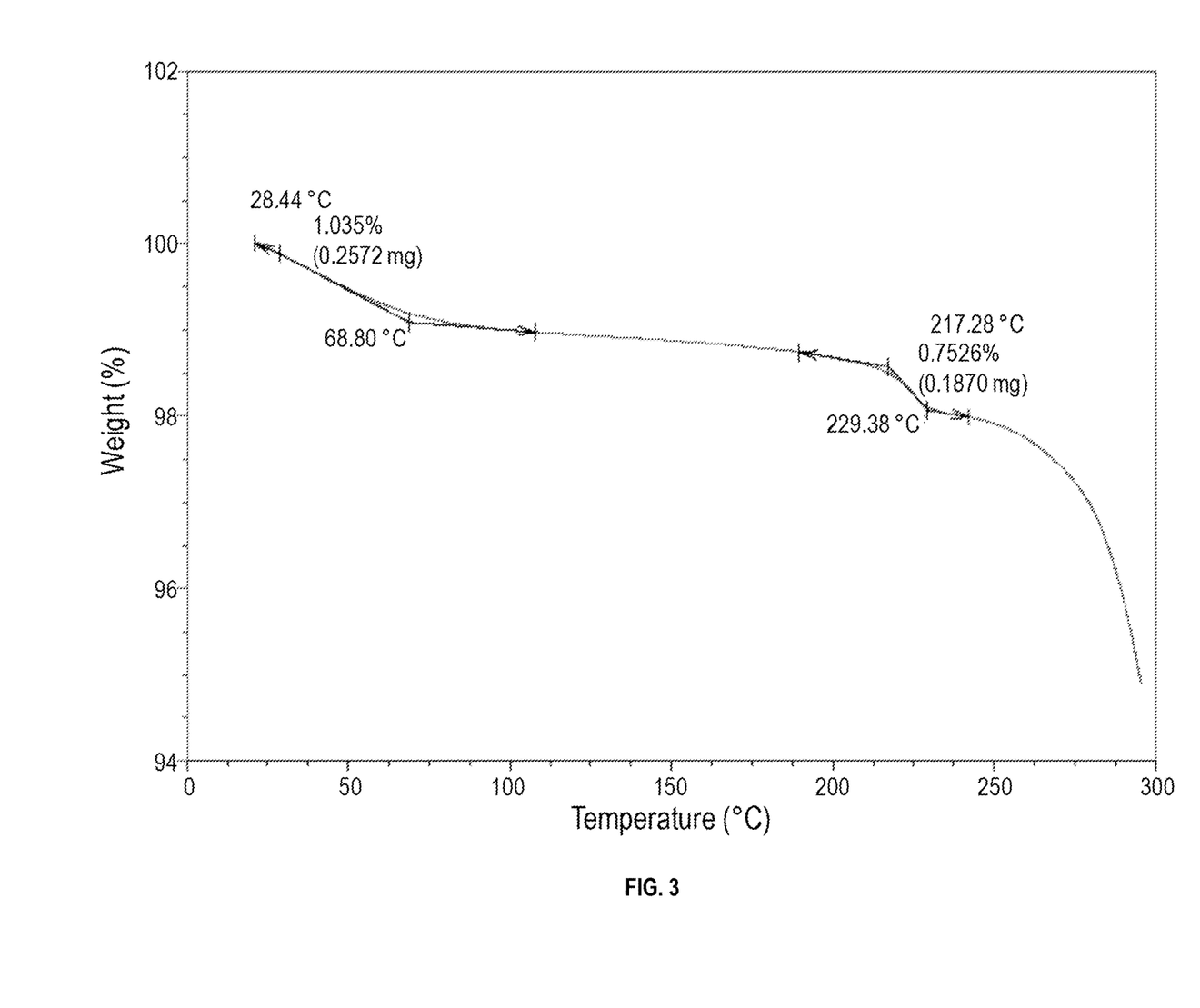
FIG. 3 is a graph illustrating the results of thermogravimetric analysis (TGA) of crystalline form A of 4-[3-(3-[(cyclopropylamino)methyl]azetidine-1-carbonyl)-4-fluorobenzyl]phthalazin-1(2H)-one hydrochloride prepared in Example 1.

The results of XRPD, DSC, and TGA of the obtained Crystalline Form A are shown in FIGS. 1, 2, and 3, respectively.

The locations of peaks of Crystalline Form A and the relative intensities thereof are represented in the following table.

TABLE 1

| Peak location (2θ) | Relative intensity (I/Io %) |
|---|---|
| 9.1° | 38.4 |
| 11.9° | 18.2 |
| 13.2° | 32.6 |
| 13.7° | 64.4 |
| 15.9° | 65.6 |
| 16.8° | 40.0 |
| 18.1° | 37.4 |
| 23.2° | 40.6 |
| 24.1° | 100.0 |
| 25.5° | 30.1 |
| 26.6° | 48.9 |

Example 2: Preparation of Crystalline Form A of 4-[3-(3-[(cyclopropylamino)methyl]azetidine-1-carbonyl)-4-fluorobenzyl]phthalazin-1(2H)-one hydrochloride 20.0 mL of acetone was added to 1.0 g of 4-[3-(3-[(cyclopropylamino)methyl]azetidine-1-carbonyl)-4-fluorobenzyl]phthalazin-1 (2H)-one, and then mixed together and cooled down to 0° C. Subsequently, after 0.2 mL of a 37.0% aqueous hydrochloric acid solution was added thereto, the temperature was raised to room temperature, and the resultant mixture was stirred for 12 hours. After cooling to 15° C., the mixture was additionally stirred for 30 minutes. The solid thus obtained was filtered, washed with acetone, and then dried to thereby obtain 0.89 g of 4-[3-(3-[(cyclopropylamino)methyl]azetidine-1-carbonyl)-4-fluorobenzyl]phthalazin-1 (2H)-one hydrochloride Crystalline Form A. (Yield: 81.7%, DSC maximum peak temperature at a heating rate of 10° C./min: 223.26° C.).

Figure 4:
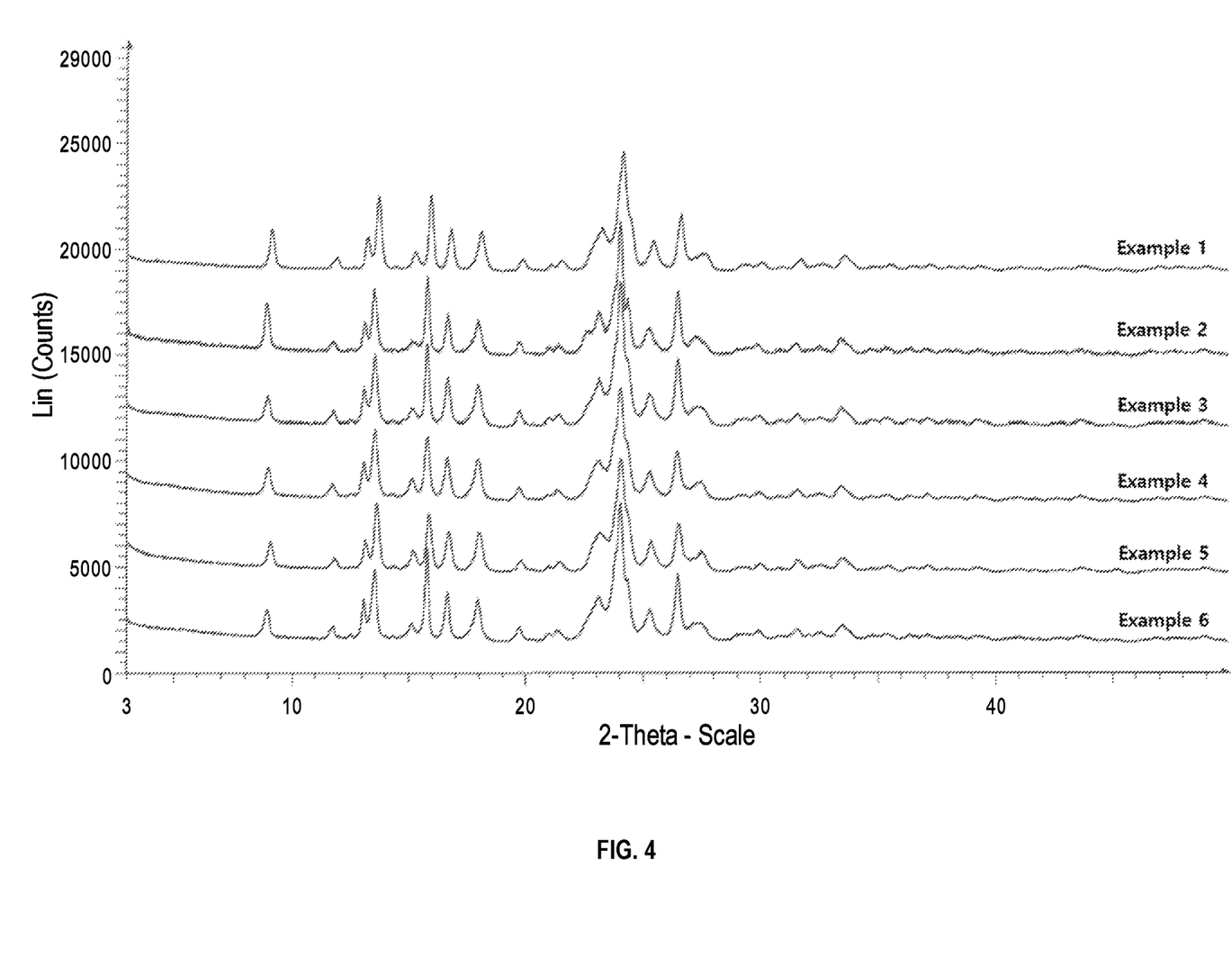
FIG. 4 is a comparative graph illustrating XRPD patterns of crystalline form A of 4-[3-(3-[(cyclopropylamino)methyl]azetidine-1-carbonyl)-4-fluorobenzyl]phthalazin-1(2H)-one hydrochloride prepared in Example 1 to Example 6.

The results of XRPD of the obtained Crystalline Form A are shown in FIG. 4.

Example 3: Preparation of Crystalline Form A of 4-[3-(3-[(cyclopropylamino)methyl]azetidine-1-carbonyl)-4-fluorobenzyl]phthalazin-1(2H)-one hydrochloride 10.0 mL of ethyl alcohol was added to 1.0 g of 4-[3-(3-[(cyclopropylamino)methyl]azetidine-1-carbonyl)-4-fluorobenzyl]phthalazin-1 (2H)-one, and then mixed together and cooled down to 0° C. Subsequently, after 0.2 mL of a 37.0% aqueous hydrochloric acid solution and 5.0 mL of ethyl alcohol were mixed together and then added to the reaction solution, the temperature was raised to room temperature, and the resultant mixture was stirred for 12 hours. After cooling to 15° C., the mixture was additionally mixed for 30 minutes. The solid thus obtained was filtered, washed with ethyl alcohol, and then dried to thereby obtain 0.57 g of Crystalline Form A of 4-[3-(3-[(cyclopropylamino)methyl]azetidine-1-carbonyl)-4-fluorobenzyl]phthalazin-1 (2H)-one hydrochloride. (Yield: 52.3%, DSC maximum peak temperature: 219.26° C.).

The results of XRPD of the obtained Crystalline Form A are shown in FIG. 4.

Example 4: Preparation of Crystalline Form A of 4-[3-(3-[(cyclopropylamino)methyl]azetidine-1-carbonyl)-4-fluorobenzyl]phthalazin-1(2H)-one hydrochloride 15.0 mL of ethyl acetate was added to 1.0 g of 4-[3-(3-[(cyclopropylamino)methyl]azetidine-1-carbonyl)-4-fluorobenzyl]phthalazin-1 (2H)-one, and then mixed together and cooled down to 0° C. Subsequently, after 0.2 mL of a 37.0% aqueous hydrochloric acid solution and 5.0 mL of ethyl acetate were mixed together and then added to the reaction solution, the temperature was raised to room temperature, and the mixture was stirred for 12 hours. After cooling down to 15° C., the mixture was additionally stirred for 30 minutes. After the thus obtained solid was filtered, washed with ethyl acetate, and then dried to thereby obtain 0.93 g of Crystalline Form A of 4-[3-(3-[(cyclopropylamino)methyl]azetidine-1-carbonyl)-4-fluorobenzyl]phthalazin-1 (2H)-one hydrochloride (Yield: 85.3%, DSC maximum peak temperature at a heating rate of 10° C./min: 222.08° C.).

The results of XRPD of the obtained Crystalline Form A are shown in FIG. 4.

Example 5: Preparation of Crystalline Form A of 4-[3-(3-[(cyclopropylamino)methyl]azetidine-1-carbonyl)-4-fluorobenzyl]phthalazin-1(2H)-one hydrochloride 15.0 mL of isopropyl alcohol was added to 1.0 g of 4-[3-(3-[(cyclopropylamino)methyl]azetidine-1-carbonyl)-4-fluorobenzyl]phthalazin-1 (2H)-one, and then mixed together and cooled down to 0° C. Subsequently, after 0.2 mL of a 37.0% aqueous hydrochloric acid solution and 5.0 mL of isopropyl alcohol were mixed together and then added to the reaction solution, the temperature was raised to room temperature, and the mixture was stirred for 12 hours. After cooling down to 15° C., the mixture was additionally mixed for 30 minutes. The solid thus obtained was filtered, then washed with isopropyl alcohol, and then dried to thereby obtain 0.96 g of 4-[3-(3-[(cyclopropylamino)methyl]azetidine-1-carbonyl)-4-fluorobenzyl]phthalazin-1 (2H)-one hydrochloride Crystalline Form A (Yield: 88.1%, DSC maximum peak temperature at a heating rate of 10° C./min: 223.81° C.).

The results of XRPD of the obtained Crystalline Form A are shown in FIG. 4.

Example 6: Preparation of Crystalline Form A of 4-[3-(3-[(cyclopropylamino)methyl]azetidine-1-carbonyl)-4-fluorobenzyl]phthalazin-1(2H)-one hydrochloride 10.0 mL of methyl alcohol was added to 1.0 g of 4-[3-(3-[(cyclopropylamino)methyl]azetidine-1-carbonyl)-4-fluorobenzyl]phthalazin-1 (2H)-one, and then mixed together and cooled down to 0° C. Subsequently, after 0.2 mL of a 37.0% aqueous hydrochloric acid solution was added to the reaction solution, and then 15.0 mL of methyl tert-butyl ether was added thereto, the temperature was raised to room temperature, and the mixture was stirred for 12 hours. After cooling to 15° C., the mixture was additionally stirred for 30 minutes. The solid thus obtained was filtered, then washed with acetone, and then dried to thereby obtain 0.95 g of 4-[3-(3-[(cyclopropylamino)methyl]azetidine-1-carbonyl)-4-fluorobenzyl]phthalazin-1 (2H)-one hydrochloride Crystalline Form A (Yield: 87.2%, DSC maximum peak temperature at a heating rate of 10° C./min: 225.02° C.).

The results of XRPD of the obtained Crystalline Form A are shown in FIG. 4.

Preparation of Crystalline Form C of Compound of Formula 1

Example 7: Preparation of Crystalline Form C of 4-[3-(3-[(cyclopropylamino)methyl]azetidine-1-carbonyl)-4-fluorobenzyl]phthalazin-1(2H)-one hydrochloride 10.0 mL of dichloromethane was added to 1.0 g of 4-[3-(3-[(cyclopropylamino)methyl]azetidine-1-carbonyl)-4-fluorobenzyl]phthalazin-1 (2H)-one, and then mixed together and cooled down to 0° C. Subsequently, after 0.2 mL of a 37.0% aqueous hydrochloric acid solution was added thereto, the temperature was raised to room temperature, followed by stirring for 12 hours. After cooling to 15° C., the mixture was additionally stirred for 30 minutes. The solid thus obtained was filtered, washed with acetone, and then dried to obtain 1.07 g of 4-[3-(3-[(cyclopropylamino)methyl]azetidine-1-carbonyl)-4-fluorobenzyl]phthalazin-1 (2H)-one hydrochloride Crystalline Form C (Yield: 98.1%, DSC maximum peak temperature at a heating rate of 5° C./min: 214.60° C.).

Figure 6:
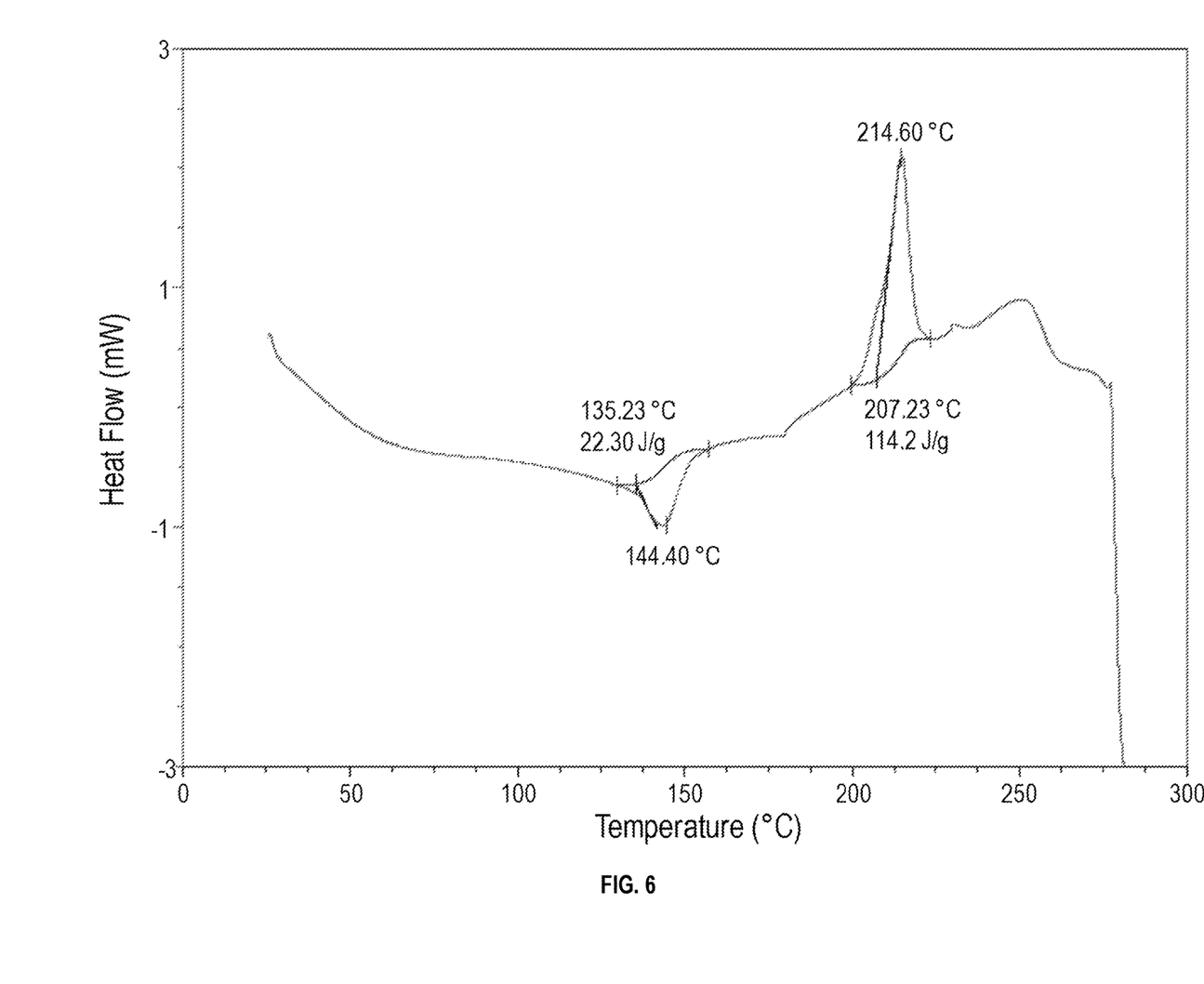
FIG. 6 is a graph illustrating the results of DSC of crystalline form C of 4-[3-(3-[(cyclopropylamino)methyl]azetidine-1-carbonyl)-4-fluorobenzyl]phthalazin-1 (2H)-one hydrochloride.
Figure 7:
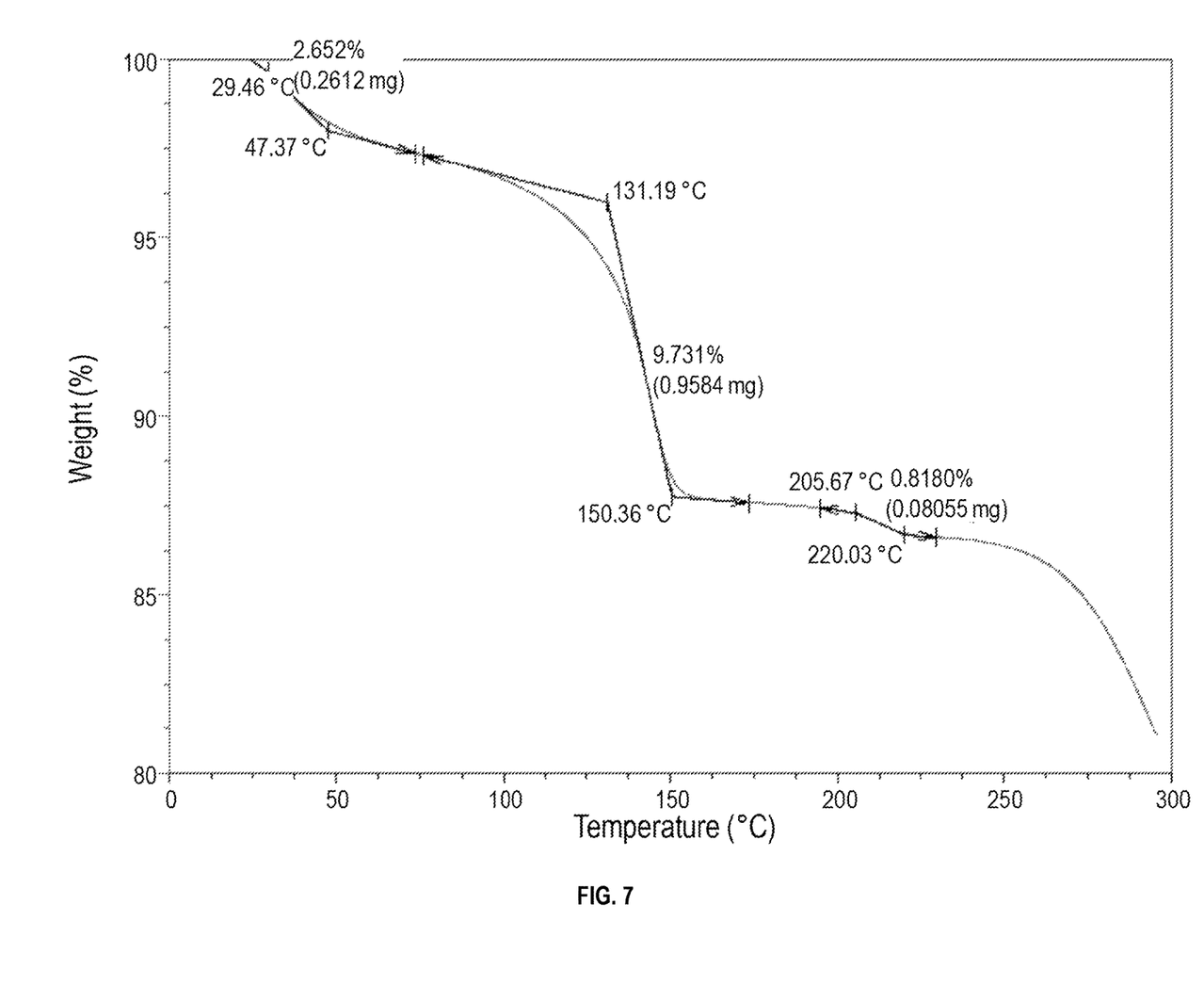
FIG. 7 is a graph illustrating the results of TGA of crystalline form C of 4-[3-(3-[(cyclopropylamino)methyl]azetidine-1-carbonyl)-4-fluorobenzyl]phthalazin-1 (2H)-one hydrochloride.

The XRPD, DSC, and TGA graphs of Crystalline Form C of Example 7 are shown in FIGS. 5, 6, and 7, respectively. The locations of characteristic peaks of Crystalline Form C and the relative intensities thereof are represented in Table 2 below.

TABLE 2

| Peak location (2θ) | Relative intensity (I/Io %) |
|---|---|
| 3.5 | 100.0 |
| 7.1 | 28.1 |
| 12.9 | 47.9 |
| 21.6 | 45.3 |
| 24.4 | 69.3 |
| 25.3 | 70.9 |

Example 8: Preparation of Crystalline Form C of 4-[3-(3-[(cyclopropylamino)methyl]azetidine-1-carbonyl)-4-fluorobenzyl]phthalazin-1(2H)-one hydrochloride 12.0 mL of methyl alcohol and 6.0 mL of dichloromethane were added to 1.0 g of 4-[3-(3-[(cyclopropylamino)methyl]azetidine-1-carbonyl)-4-fluorobenzyl]phthalazin-1 (2H)-one, and then mixed together and cooled down to 0° C. Subsequently, after 2.5 mL of 1.0 M hydrochloric acid solution in ethyl acetate was added to the reaction solution, the temperature was raised to room temperature, followed by stirring for 5 hours. After cooling to 15° C., the mixture was additionally stirred for 30 minutes. The solid thus obtained was filtered, washed with methyl alcohol, and then dried to obtain 0.70 g of 4-[3-(3-[(cyclopropylamino)methyl]azetidine-1-carbonyl)-4-fluorobenzyl]phthalazin-1 (2H)-one hydrochloride Crystalline Form C (Yield: 64.2%, DSC maximum peak temperature at a heating rate of 10° C./min: 223.34° C.).

Example 9: Preparation of Crystalline Form C of 4-[3-(3-[(cyclopropylamino)methyl]azetidine-1-carbonyl)-4-fluorobenzyl]phthalazin-1(2H)-one hydrochloride 12.0 mL of methyl alcohol and 6.0 mL of dichloromethane were added to 1.0 g of 4-[3-(3-[(cyclopropylamino)methyl]azetidine-1-carbonyl)-4-fluorobenzyl]phthalazin-1(2H)-one, and then mixed together and cooled down to 0° C. Subsequently, after 2.5 mL of 1.0 M hydrochloric acid solution in diethyl ether was added to the reaction solution, the temperature was raised to room temperature, followed by stirring for 5 hours. After cooling to 15° C., the mixture was additionally stirred for 30 minutes. The solid thus obtained was filtered, washed with methyl alcohol, and then dried to obtain 0.68 g of 4-[3-(3-[(cyclopropylamino)methyl]azetidine-1-carbonyl)-4-fluorobenzyl]phthalazin-1 (2H)-one hydrochloride Crystalline Form C (Yield: 62.4%, DSC maximum peak temperature at a heating rate of 10° C./min: 222.36° C.).

Example 10: Preparation of Crystalline Form C of 4-[3-(3-[(cyclopropylamino)methyl]azetidine-1-carbonyl)-4-fluorobenzyl]phthalazin-1(2H)-one hydrochloride 12.0 mL of methyl alcohol and 6.0 mL of dichloromethane were added to 1.0 g of 4-[3-(3-[(cyclopropylamino)methyl]azetidine-1-carbonyl)-4-fluorobenzyl]phthalazin-1(2H)-one, and then mixed together and cooled down to 0° C. Subsequently, after 0.5 mL of 5 to 6 N hydrochloric acid solution in isopropyl alcohol was added to the reaction solution, the temperature was raised to room temperature, followed by stirring for 5 hours. After cooling to 15° C., the mixture was additionally stirred for 30 minutes. The solid thus obtained was filtered, washed with acetone, and then dried to obtain 0.65 g of 4-[3-(3-[(cyclopropylamino)methyl]azetidine-1-carbonyl)-4-fluorobenzyl]phthalazin-1 (2H)-one hydrochloride Crystalline Form C (Yield: 59.6%, DSC maximum peak temperature at a heating rate of 10° C./min: 222.45° C.).

Example 11: Preparation of Crystalline Form C of 4-[3-(3-[(cyclopropylamino)methyl]azetidine-1-carbonyl)-4-fluorobenzyl]phthalazin-1(2H)-one hydrochloride 12.0 mL of methyl alcohol and 6.0 mL of dichloromethane were added to 1.0 g of 4-[3-(3-[(cyclopropylamino)methyl]azetidine-1-carbonyl)-4-fluorobenzyl]phthalazin-1 (2H)-one, and then mixed together and cooled down to 0° C. Subsequently, after 2.0 mL of 1.25 M hydrochloric acid solution in ethyl alcohol was added to the reaction solution, the temperature was raised to room temperature, followed by stirring for 5 hours. After cooling to 15° C., the mixture was additionally stirred for 30 minutes. The solid thus obtained was filtered, washed with acetone, and then dried to obtain 0.43 g of 4-[3-(3-[(cyclopropylamino)methyl]azetidine-1-carbonyl)-4-fluorobenzyl]phthalazin-1 (2H)-one hydrochloride Crystalline Form C (Yield: 39.5%, DSC maximum peak temperature at a heating rate of 10° C./min: 221.16° C.).

It was confirmed from Examples 7-11 that Crystalline Form C was obtained when using dichloromethane alone or the mixture solvent of dichloromethane and methanol, in any type of hydrochloric acid.

Preparation of Amorphous Form of Compound of Formula 1

Examples 12 Preparation of Amorphous Form of 4-[3-(3-[(cyclopropylamino)methyl]azetidine-1-carbonyl)-4-fluorobenzyl]phthalazin-1(2H)-one hydrochloride 90.0 mL of methyl alcohol was added to 1.0 g of 4-[3-(3-[(cyclopropylamino)methyl]azetidine-1-carbonyl)-4-fluorobenzyl]phthalazin-1 (2H)-one hydrochloride, and then mixed together and concentrated. 20.0 mL of acetone was rapidly added into the concentrated residual to result in a crystal, followed by concentrating. 15.0 mL of n-heptane was added into the concentrated residual, stirred for 5 minutes, and filtered to obtain 0.75 g of 4-[3-(3-[(cyclopropylamino)methyl]azetidine-1-carbonyl)-4-fluorobenzyl]phthalazin-1(2H)-one hydrochloride Amorphous Form (Yield: 75.0%).

The results of XRPD of the obtained amorphous form are shown in FIG. 8.

The obtained amorphous form readily absorbed water during the storage, i.e., it was hygroscopic, whereby the color turned yellow. It was thus confirmed that the amorphous form was not suitable for use as a medicinal drug substance.

Experimental Example 1: Stability Test of Crystalline Form A

Crystalline Form A of the compound of Formula 1 prepared in Example 1 was stored under long-term storage conditions (25±2° C., and Relative humidity: 60±5%). Samples were taken after 3 months, 6 months, 9 months, 12 months, 18 months, and even 24 months from the onset of the storage to measure total impurities content by high performance liquid chromatography (HPLC). The results are shown in Table 3.

TABLE 3

Results of long-term stability purity test of Crystalline Form A

| Storage period | Initial | 3 months | 6 months | 9 months | 12 months | 18 months | 24 months |
|---|---|---|---|---|---|---|---|
| Total impurities content (wt %) | 0.14% | 0.15% | 0.16% | 0.15% | 0.14% | 0.19% | 0.20% |

As such, the above results indicate that Crystalline Form A of the compound of Formula 1 exhibits high stability under long-term storage conditions. Thus, Crystalline Form A is desirable for use as a medicinal drug substance.

Those of ordinary skill in the art will recognize that the present invention may be embodied in other specific forms without departing from its spirit or essential characteristics. The described embodiments are to be considered in all respects only as illustrative and not restrictive. The scope of the present invention is, therefore, indicated by the appended claims rather than by the foregoing description. All changes which come within the meaning and range of equivalency of the claims are to be embraced within the scope of the present invention.

The invention claimed is:

1. A pharmaceutical composition comprising a crystalline form of a compound of Formula 1, exhibiting an X-ray powder diffraction (XRPD) pattern comprising peaks at 2θ±0.2° values of 13.7°, 15.9°, and 24.10:

[Formula 1]

as an active ingredient and at least one pharmaceutically acceptable carrier or diluent.

2. The pharmaceutical composition of claim 1, wherein the crystalline form makes up 80% or more of a total amount of the compound of Formula 1 in the pharmaceutical composition.

3. The pharmaceutical composition of claim 1, wherein the pharmaceutical composition is for the treatment of cancer.

4. The pharmaceutical composition of claim 3, wherein the cancer is caused by a genetic defect in the BRCA1 or BRCA2 genes.

5. The pharmaceutical composition of claim 3, wherein the cancer is selected from the group consisting of breast cancer, ovarian cancer, pancreatic cancer, gastric cancer, lung cancer, colon cancer, brain tumor, prostate cancer, and Ewing's sarcoma.

* * * * *